US006187095B1

(12) United States Patent
Labrecque et al.

(10) Patent No.: US 6,187,095 B1
(45) Date of Patent: Feb. 13, 2001

(54) PROCESS AND APPARATUS FOR COATING SURGICAL SUTURES

(76) Inventors: Samsel K. Labrecque, 3521 Thompson Bend, Gainesville, GA (US) 30506; Vishvaroop Agarwal, 290 River Rd. #C11, Piscataway, NJ (US) 08854; Henry Pokropinski, Jr., 42 Lake Ave., Helmetta, NJ (US) 08828

( * ) Notice: Under 35 U.S.C. 154(b), the term of this patent shall be extended for 0 days.

(21) Appl. No.: 09/073,093

(22) Filed: May 5, 1998

Related U.S. Application Data

(62) Division of application No. 08/741,842, filed on Oct. 31, 1996, now Pat. No. 5,817,129.

(51) Int. Cl.[7] .............................. B05C 11/02; B05C 3/12
(52) U.S. Cl. ........................ 118/110; 118/420; 118/423; 118/DIG. 19
(58) Field of Search ..................... 118/420, 124, 118/429, DIG. 19, 401, 110, DIG. 15, 423, 428, 234; 68/19; 8/151.2

(56) References Cited

U.S. PATENT DOCUMENTS

| 2,022,854 | 12/1935 | Greenwood | 91/38 |
|---|---|---|---|
| 2,262,793 | 11/1941 | Bruenger | 34/75 |
| 3,045,315 | 7/1962 | Dusenbury | 28/59.5 |
| 3,857,261 | 12/1974 | Wilcox | 68/22 |
| 3,942,532 | 3/1976 | Hunter et al. | 128/335.5 |
| 3,980,177 | 9/1976 | McGregor | 206/63.3 |
| 3,982,543 | 9/1976 | Schmitt et al. | 128/335.5 |
| 4,047,533 | 9/1977 | Perciaccante et al. | 128/335.5 |
| 4,105,034 | 8/1978 | Shalaby et al. | 128/335.5 |
| 4,201,216 | 5/1980 | Mattel | 128/335.5 |
| 4,241,690 | 12/1980 | Muller | 118/63 |
| 4,626,306 | * 12/1986 | Chabrier et al. | 156/180 |
| 4,711,241 | 12/1987 | Lehman | 128/335.5 |
| 4,716,203 | 12/1987 | Casey et al. | 525/408 |
| 4,857,602 | 8/1989 | Casey et al. | 525/408 |
| 4,994,074 | 2/1991 | Bezwada et al. | 606/230 |
| 5,037,950 | 8/1991 | Bezwada et al. | 528/354 |
| 5,089,013 | 2/1992 | Bezwada et al. | 606/228 |
| 5,100,433 | 3/1992 | Bezwada et al. | 606/230 |
| 5,102,420 | 4/1992 | Hunter et al. | 606/231 |
| 5,104,398 | 4/1992 | Planck et al. | 606/230 |
| 5,123,912 | 6/1992 | Kaplan et al. | 606/230 |
| 5,147,382 | 9/1992 | Gertzman et al. | 606/228 |
| 5,366,081 | 11/1994 | Kaplan et al. | 206/339 |
| 5,371,176 | 12/1994 | Bezwada et al. | 528/354 |
| 5,403,347 | 4/1995 | Roby et al. | 606/230 |
| 5,431,679 | 7/1995 | Bennett et al. | 606/230 |
| 5,442,032 | 8/1995 | Arnold et al. | 528/354 |
| 5,447,100 | 9/1995 | Chesterfield et al. | 100/161 |
| 5,462,162 | 10/1995 | Kaplan et al. | 206/339 |
| 5,468,252 | 11/1995 | Kaplan et al. | 606/228 |
| 5,472,702 | 12/1995 | Muth et al. | 606/228 |

* cited by examiner

Primary Examiner—Richard Crispino
Assistant Examiner—George R Koch, III

(57) ABSTRACT

The present invention provides a process and apparatus for coating sutures.

11 Claims, 4 Drawing Sheets

PROCESS AND APPARATUS FOR COATING SURGICAL SUTURES

This application is a divisional application of U.S. Ser. No. 08/741,842, filed Oct. 31, 1996, now U.S. Pat. No. 5,817,129.

FIELD OF THE INVENTION

This invention relates to a process for coating surgical ligatures such as sutures and an apparatus for coating surgical ligatures.

BACKGROUND OF THE INVENTION

Sutures are generally coated with a lubricious coating to improve the tie down and knot adjustability of the suture. Additionally, these coatings may also reduce the drag associated with passing the suture through the tissue thereby reducing the tissue trauma.

The coatings that are applied to sutures generally contain a biocompatable polymer and optionally other additives such as, fatty acid salts or esters may be added into the coating to further improve the lubricity of the coated sutures. These coatings are usually dissolved or suspended in a volatile organic liquid and applied in the form of a liquid coating to the sutures. Conventionally these liquid coatings have been applied by dip coating, bushing, wiping, drip coating, spray coating or by using a coating/filling head. Sutures can be dip coated in a batch process by winding a suture on a frame and immersing the frame into a coating solution or in a continuous process in which the suture is passed under tension into a dip tank then through a drying tunnel (as described in U.S. Pat. No. 3,982,543). In a continuous dip coating process sutures are generally coated at a rate of about 45–60 feet per minute. Another means of coating sutures is to drip coat a suture using a syringe pump to apply the coating to a moving suture. Sutures can be drip coated at about 44 meters per minute, (described in U.S. Pat. No. 5,472,702 column 7, lines 1–20). Coating/filling heads have also been used to coat sutures, such as the filling heads described in U.S. Pat. No. 5,447,100. The speed at which sutures are coated using these filling heads is about 50 meters per minute (see column 14, line 58 of U.S. Pat. 5,447,100).

Although the coating process that have been conventionally used provide acceptable coatings for sutures, the production speeds at which the coatings are applied are very low. Therefore, it would be a significant contribution to the art of suture production to provide a faster means for coating sutures.

SUMMARY OF THE INVENTION

We have discovered a suture coating apparatus comprising a vessel suitable for containing a coating mixture having an opening suitable for passing a suture through; a first guide means for directing a suture into the coating mixture contained in the vessel; a second guide means positioned in said vessel suitable for redirecting the suture out of the coating mixture; a third guide means suitable for redirecting a suture through at least about a 90 degree turn; wherein the suture travels at a speed sufficient to remove any excess coating entrained by the suture when it is redirected by the third guide means.

We have discovered a suture coating apparatus comprising a vessel suitable for containing a coating mixture having an opening suitable for passing a suture through; a first guide means for directing a suture into the coating mixture contained in the vessel; a second guide means positioned in said vessel suitable for redirecting the suture out of the coating mixture; a third guide means having a surface which is adjacent to or contacts the suture and forms a meniscus that remove any excess coating entrained by the suture when it is redirected by the third guide means.

We have also discovered a continuous process for coating sutures comprising in a continuous process contacting a suture with a coating mixture (which for the purpose of this invention includes solutions, dispersion, emulsions, suspensions and the like) to provide a wet coated suture; removing the wet coated suture from the coating mixture and completely or partially preventing the excess coating mixture on the wet coated suture from contacting the coating mixture thereby maintaining the coating mixture at a substantially constant concentration; and drying the wet coated suture to provide a coated suture.

In another embodiment of the present invention we have discovered a suture coating head comprising a vessel suitable for containing a coating mixture having an opening suitable for passing a suture through; a first guide means for directing a suture from a substantially vertical downward path to a substantially vertical upward path, said first guide means being positioned in said vessel; and a fluid impermeable diverter being positioned to control fluid communications from a suture as the suture exits the vessel.

DETAILED DESCRIPTION

Figure 1:
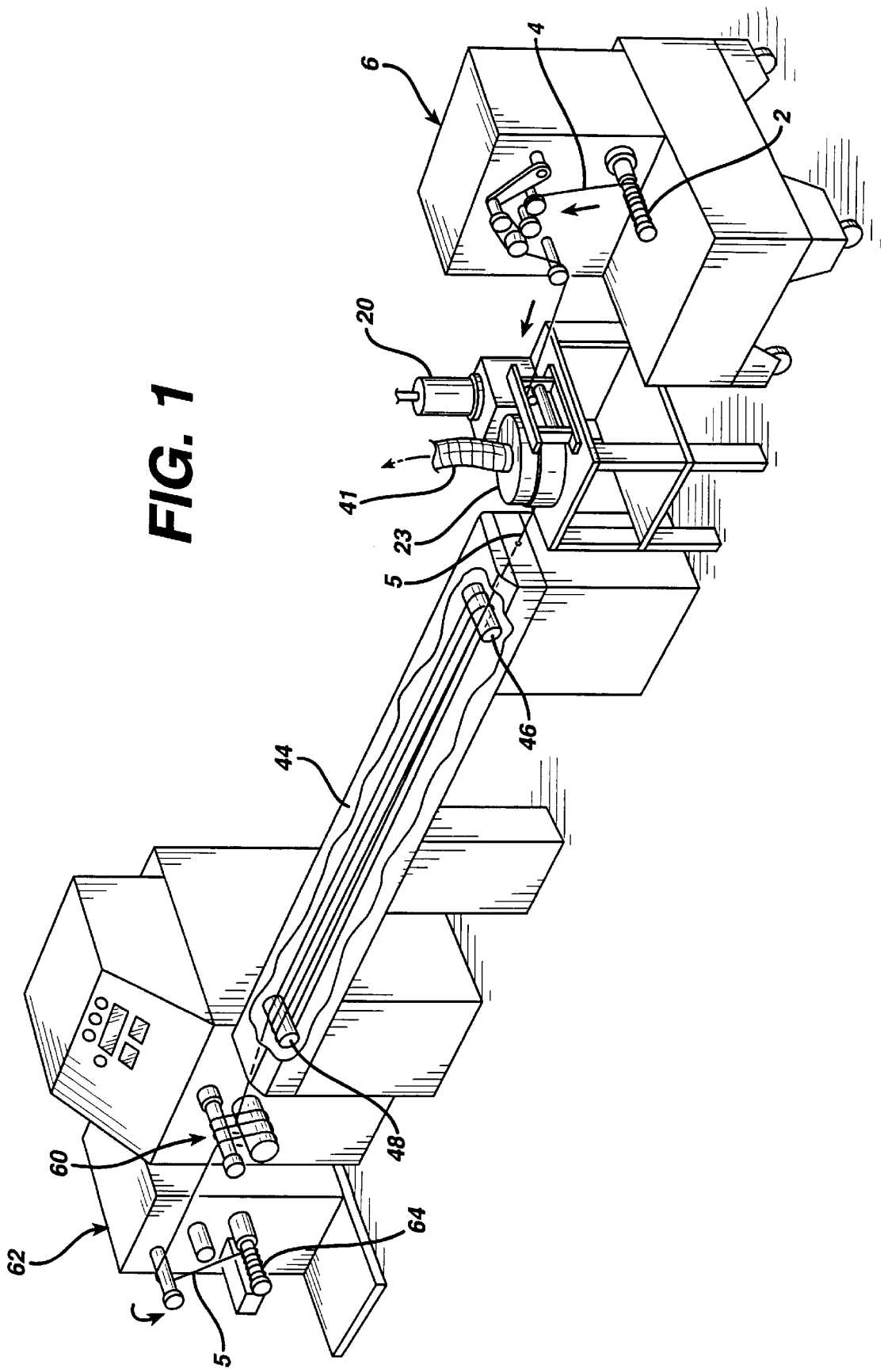
FIG. 1 illustrates one embodiment of a coating line suitable for coating a surgical suture.
Figure 2:
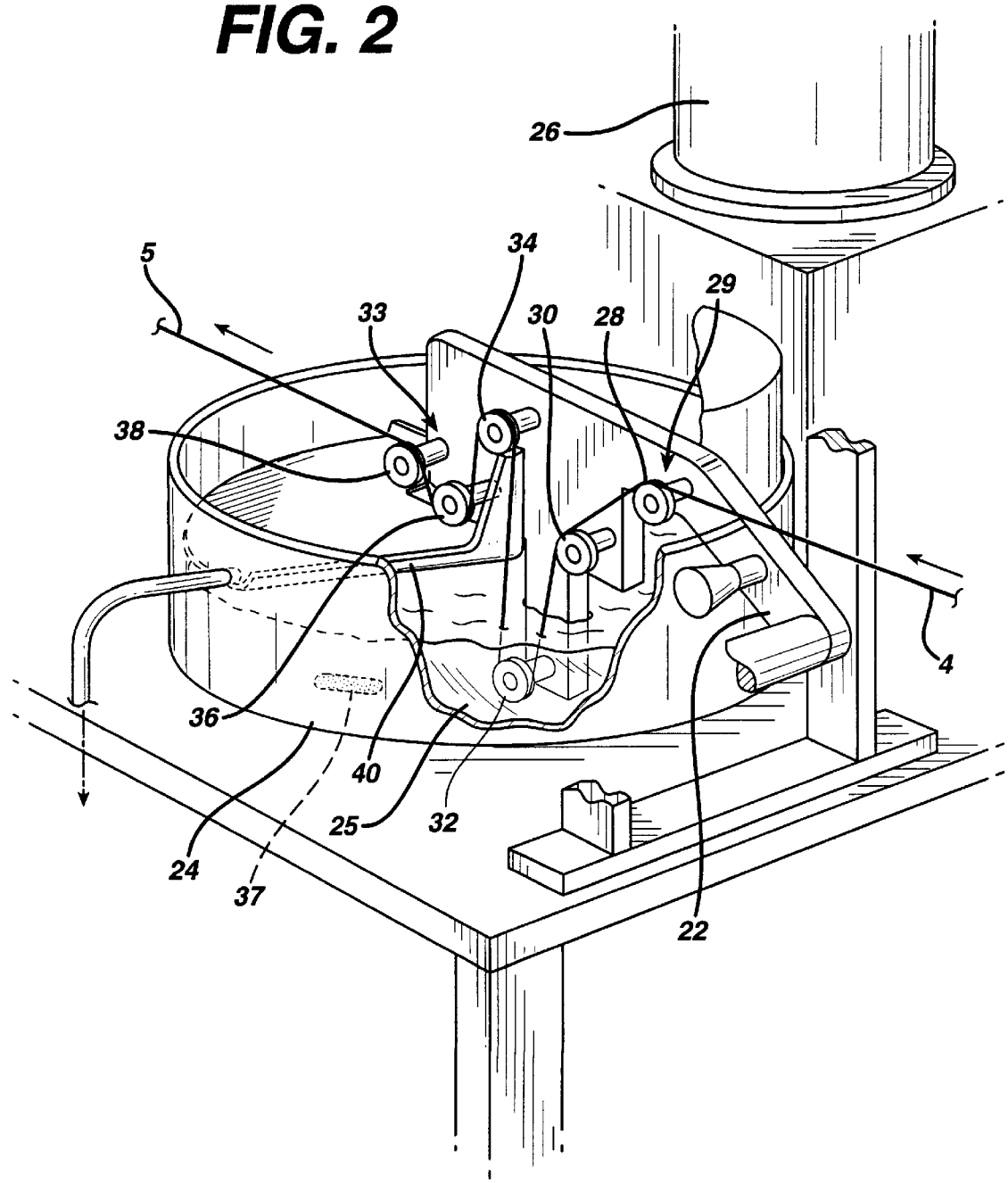
FIG. 2 illustrates a coating head which is suitable for coating a surgical suture.

The inventive system for coating sutures is illustrated in FIG. 1. As shown in FIG. 1 a spool 2 of suture 4 is placed on let off device 6. The suture 4 travels from let off device 6 to the coating head 20 as shown in FIG. 2. The coating head 20 comprises a support 22 to which are attached a first guide means 30 and second guide means 32 (which as illustrated comprise guide rollers but may include wire loops or pigtails) for directing the suture 4 into the coating mixture 25 contained in vessel 24 and preferably secured in position relative to said vessel 24. The guide rollers are made of a nontoxic nonreactive material which is inert to the solvents employed in the coating mixture. Preferably the guides rollers will be coated with a nonreactive material such as a ceramic, or stainless steel alloy (such as the rollers manufactured by Yuasa of Japan). The first guide means 30 redirect the suture 4 from a horizontal path to a path which is substantially vertical and downward. The first guide means 30 may be associated with one or more additional guide means (as illustrated in FIG. 2 guide roller 28) which reorients the suture to a substantially vertical path. The suture 4 then travels from the first guides means 30 to a second guide means 32 which orients the suture 4 to a substantially vertical path which is upward (which is preferably perpendicular to the surface of the coating mixture). The second guide means 32 may be associated with a third guide means 34. The third guide means 34 may be associated with one or more auxiliary guide means to further reorient the suture such as guide means 36 and 38.

As the suture passes from the guide roller 30 to guide roller 32 it is submerged in coating mixture 25 and is coated with the coating mixture 25 to provide a wet coated suture 5. After the wet coated suture 5 has been reoriented by the guide roller 32 it emerges from the coating mixture 25 as a wet coated suture 5 and is turned through a sharp turn which is designed to generate sufficient centrifugal force to remove the excess coating mixture entrained with the suture. The angle and radius of the turn will vary depending on the composition and density of the coating mixture, the speed that the suture is moving, the viscosity of the coating mixture and the size of the suture. Currently it is preferably for sizes 0 to 8–0 suture that the turn be at least about 120 degree turn by guide means 34 and preferably through at least about 160 degree turn suture (using the preferred calcium stearate, film-forming polymer mixture in ethyl acetate).

Figure 3:
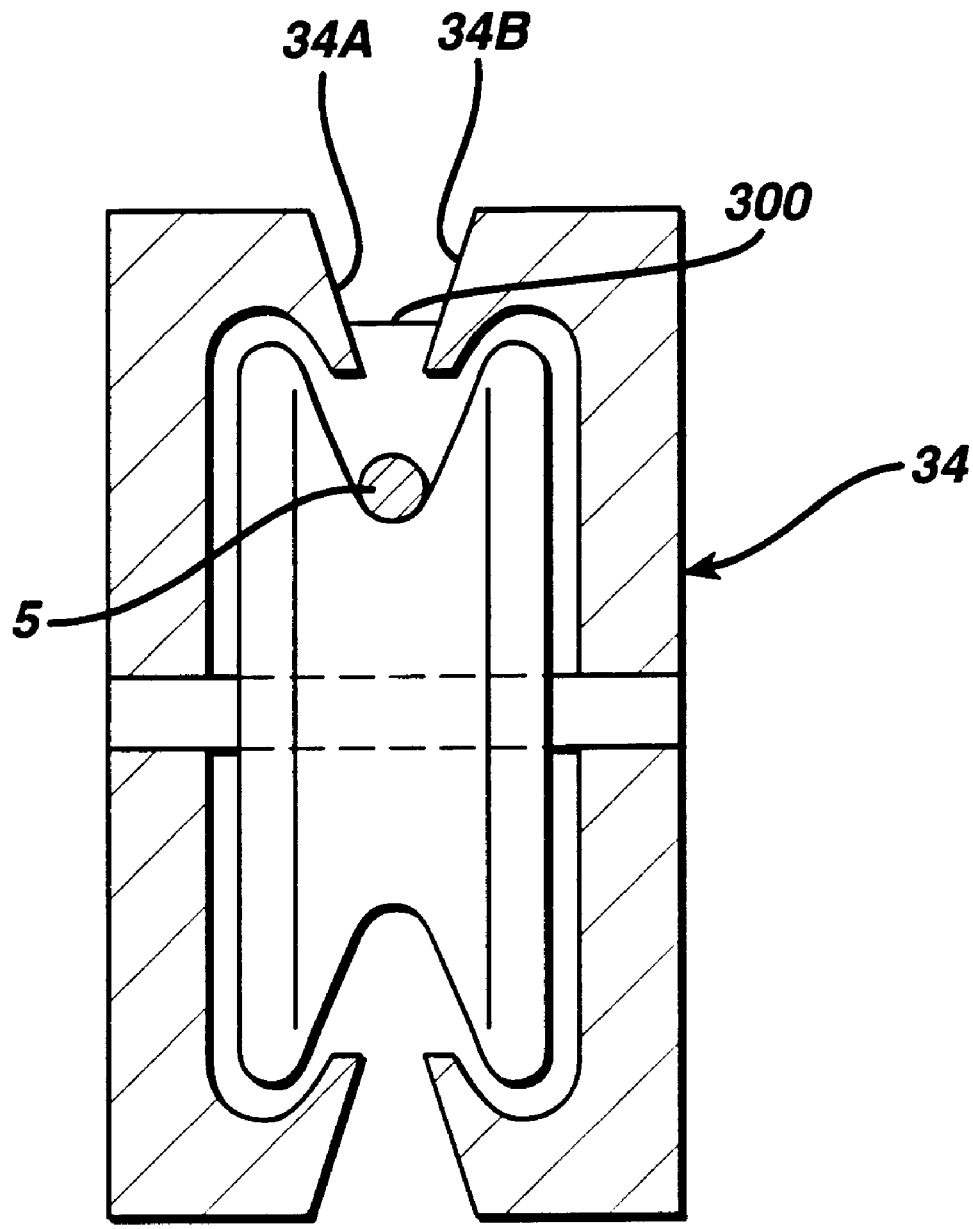
FIG. 3 illustrates a cross-section of one embodiment of guide means.

Alternatively, the excess coating may be removed from the surface of the suture after it emerges from contacting the coating by positioning a surface in close proximity (adjacent) to the path of the suture or in contact with the suture as it exits the vessel. The surface should be placed close enough to the surface of the suture to form a meniscus with the wet coated suture. The meniscus will facilitate the removal of the excess coating mixture and may have various geometries from a rounded point to a flat surface. In one embodiment of the invention it is proposed to size the guide means 34 with the sides of the guide means 34A and 34B being suitable for forming a meniscus 300 and removing the excess coating mixture as shown in FIG. 3.

Guide means 34 is important for separating the excess coating mixture from the wet coated suture 5, which substantially prevents an excessive or uneven amount of coating from being deposited on the suture. Guide means 34 reorients the coated suture 5 from a vertical upward path to a path that is substantially vertical and downward. From guide roller 34 the coated suture 5 travels to guide roller 36 which reorients the coated suture 5 into a substantially horizontal path. The coated suture 5 then optionally travels to guide roller 38 which completes the orientation of the coated suture to a substantially horizontal path.

In an another embodiment of the invention when the coated suture 5 emerges from the coating mixture 25, excess coating mixture 25 is entrained with the wet coated suture 5. The excess coating mixture falls off the coated suture 5 as it travels through guide means 34 (as shown in FIG. 2). As the excess mixture drips off the coated suture 5, it is caught by a diverter 40 which partially or completely prevents it from returning to the coating mixture 25 and changing the concentration of the coating mixture 25. Maintaining a substantially constant concentration of solvent to the biocompatable polymer and optionally fatty acid is important to maintaining a uniform suture coating. The coating mixture caught by the diverter 40 may be fed to a reservoir for reconstitution and reuse or disposal. The diverter 40 significantly improves the final suture product by insuring a uniformly coated suture is produced throughout the coating process. The diverter 40 can constitute a plate that completely separates the vessel into an upper and lower section.

Figure 4:
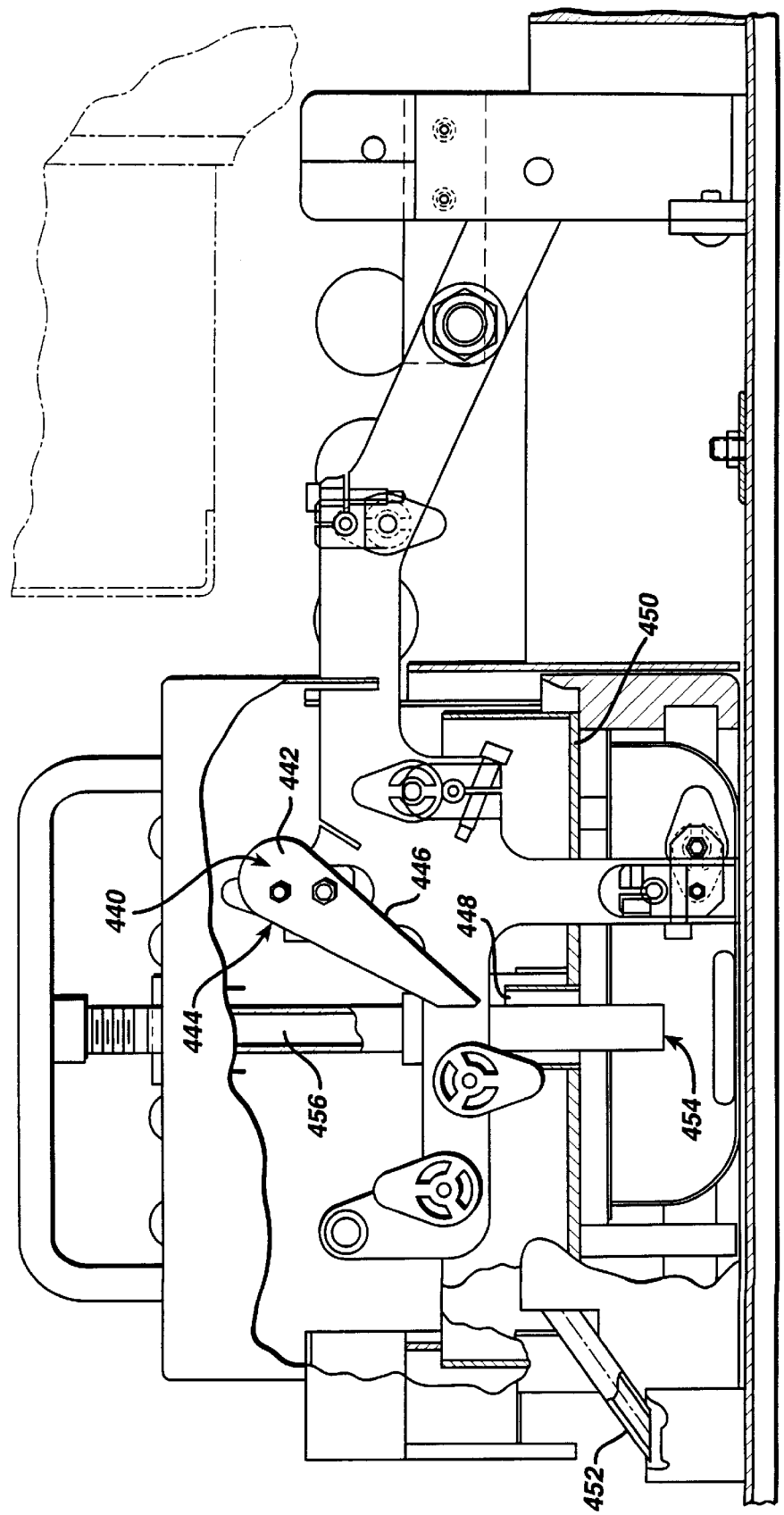
FIG. 4 illustrates an alternative embodiment of the coating head which is suitable for coating a surgical suture.

Alternatively, some of the coating mixture may be returned to the coating bath to minimize waste. However, the amount returned to coating bath must not be enough to adversely affect the concentration of the coating bath. The drip guard 440 shown in FIG. 4 provides a means for returning the excess coating mixture to the coating bath. The drip guard 440 as shown in FIG. 4 has two side members 442 and 444 attached along opposite sides of base 446. The excess coating mixture coming off of the suture at guide means 34 is directed by the drip guard 440 into the diverter. Suture lines without the drip guard 440 drip their excess directly back into the vessel 24 via the same opening in the diverter that provides access to guide means 32. The excess coating mixture not returned to the vessel is directed by diverter plate 450 to drain 452.

Additionally, the guide roller assembly shown in FIG. 2 and FIG. 4 allows sutures to be coated at processing speed of greater than 175 feet per minute and will preferably operate in the range of from about 200 to about 450 feet per minute.

The level of the coating mixture 25 in the vessel 24 is maintained at a constant level and additional coating mixture 25 is supplied by coating reservoir 26 which is in fluid communication with vessel 24 by means of an outlet in the reservoir, a conduit 456 and an inlet 454 in the vessel (as shown in FIG. 4). The vessel 24 and reservoir 26 may be equipped with a temperature controlling means, recirculating means and/or an agitating means to assure the coating mixture remains uniform (such as the magnetic stirring bar 37 shown in vessel 24). The coating mixture level in the vessel 24 may be maintained at a constant level by an automatic feed system which controls the transfer of coating mixture from the reservoir 26 to the vessel 24. A gravity feed system or mechanical system may be used for this purpose. The vessel 24 during operation may be closed or covered with a cover 23 to prevent the solvent in the coating mixture from volatilizing into the air. The cover may also be connected to a vent assembly 41 to remove solvent vapors from the work area. Alternately, the coating assembly may be enclosed in a hood or placed in close proximity to a fume remove vent.

After the wet coated suture 5 leaves the coating head 20, it proceeds to a drying tunnel 44 where the coating mixture is dried on the coated suture 5 and the solvent is substantially removed. The drying tunnel 44 should be maintained at a temperature of from about 20° C. to about 125° C., preferably in the range of from about 40° C. to about 65° C. and most preferably in the range of from about 45° C. to 55° C. The drying tunnel 44 should also have a gas flow (filtered air or other inert gas such as, nitrogen, carbon dioxide etc. with a moisture content preferably of less than 30 percent) throughout the tunnel (preferably in the opposite direction of coated suture 5) in an amount sufficient to provide the desired degree of drying in a desired amount of time. Generally the air flow will be in the range of about 25 to about 3000 cu.ft./min., preferably in the range of from about 50 to about 800 cu.ft./min. and most preferably 55 to 75 cu.ft./min. The coated suture 5 will have a residence time in the drying tunnel 44 sufficient to render the suture dry to the touch and remove substantially all the coating mixture solvent. Currently, it is preferred for the coated sutures to reside in the drying tunnel 44 or from about 1 to about 20 seconds and most preferably for from about 3 to about 7 seconds. The amount of time the coated suture 5 is in the drying tunnel can be increased by adding two turning guide such as guide rollers 46 and 48 in the drying tunnel 44 to the allow the suture to traverse the tunnel several times.

The dried suture may then be taken up on a take up spool 64, preferably the suture will first travel through a godet drive 60 to equilibrate the tension on the coated suture 5 and then it will travel to a take up winder 62.

Those skilled in the art will also appreciate that by placing additional spools on the let off device 6 and a plurality of guide means in parallel on frame 22, that several sutures could be simultaneously coated by a single coating head 20. The presence of additional sutures would also require adjustments in the air flow and a take up winder 62 capable of winding multiple spools of sutures. It is currently preferred to coat one to six sutures simultaneously.

Suture coatings generally contain one or more biocompatable polymer and optionally other additives such as fatty acid salts or esters. Suitable biocompatable suture coatings that have been suggested in the literature include nonabsorbable materials such as silicone, teflon, beeswax, polybutilate or polyetherimides, as well as, absorbable materials such as homopolymers and copolymers of glycolide, lactide (which includes L-, D-, and meso- forms of lactide and mixtures thereof), $\epsilon$-caprolactone, p-dioxanone, trimethylene carbonate, 1,4-dioxepan-2-one, polyalkylene glycols, castor oil derivatives, polyoxaesters, polyoxaamides, copolymers of vinyl acetates with unsaturated carboxylic acids (such as crotonic, acrylic, and methyacrylic acids), water soluble or dispersible cellulose derivatives (such as methyl cellulose, hydroxymethyl cellulose and carboxymethyl cellulose); natural gums; ethylene oxide polymers polyacrylamide; collagen; gelatin; polyamino acids; polyvinyl alcohol; absorbable conjugated unsaturated triglycerides such as dehydrated castor oil and mixtures of such polymers. Several of these coatings are described in one or more of the following U.S. Pat. Nos. 3,527,650 (teflon coatings); 3,942,532 (aliphatic polyesters); 4,105,034 (polyalkylene oxalates); 4,624,256 (poly $\epsilon$-caprolactone); 4,791,929 (poly $\epsilon$-caprolactone-co-glycolide); 4,994,074 (poly $\epsilon$-caprolactone-coglycolide); 5,037,950 (polyp-dioxanone-co-$\epsilon$-caprolactone); 5,102,420 (polyether-co-amides); 5,371,176 (castor oil derivatives); 5,442,032 (homopolymers and copolymers of 1,4-dioxepan-2-one); and 5,464,929 (polyoxaesters) which are all hereby incorporated herein by reference. Particularly preferred are film-forming copolymers of L-lactide and glycolide which contain from about 15 to 85 percent L-lactide, and have an inherent viscosity of from about 0.5 to 2.0 measured as a 0.1 percent mixture in hexafluorisopropanol at 25° C.

The fatty acid salts useful in the coating compositions of the present invention are biocompatible salts of fatty acids including the calcium, magnesium, barium, aluminum, and zinc salts of six carbon and higher fatty acids, particularly those having from about 12 to 22 carbon atoms and mixtures thereof. The calcium salts of stearic, palmitic and oleic acids are particularly preferred for use in the present invention.

The ratio of the polymer and the fatty acid salt in the coating composition may vary depending upon the specific components selected and the particular suture being coated. In general, the preferred ratio of polymer to salt is within the range of 2:1 to 1:2 by weight, although useful compositions are obtained over a wider range of from about 1:4 to 4:1 parts by weight.

With sutures composed of homopolymers or copolymers of lactide and glycolide, the polymers in the coating composition is preferably polylactide or a copolymer of L-lactide and glycolide containing at least about 15 percent L-lactide, and preferably having different solubility characteristics than the suture. For example, a suture made of a lactide-glycolide copolymer containing about 10 percent of lactyl moieties may be coated with a composition containing, as a biocompatable polymer, a lactide-glycolide copolymer containing about 65 percent of lactyl moieties, which copolymer is more readily soluble in the selected solvent system than the suture material.

The biocompatable polymer in the coating composition may, if desired, be the same composition as the suture provided that precautions are taken to avoid dissolving the suture when the coating composition is applied. This can be done by utilizing a coating composition in which the biocompatable polymer is in mixture at substantially saturation levels and the contact time of the suture with the coating composition is short before the solvent is driven off.

Where the compositions of the suture and the polymers in the coating are identical, and in other instances where the suture material may be subject to some surface dissolution and/or surface swelling or softening by reason of the action of the solvent thereon, there may be a gradual transition between the substrate composition and the coating composition rather than a sharp interface between them. There may also be some weakening of the suture accompanying the application of such coating compositions.

The coating composition may, if desired, also contain components other than those discussed above for other useful purposes including dyes, proteins (such as growth factors), antibiotics, antiseptics, anesthetics and anti-inflammatory agents.

Suitable solvents for these biocompatable polymers are generally volatile organic solvents such as chloroform, toluene, xylene, 1,2,2-trichloroethane and blends thereof. However, preferred are less toxic solvent such as acetone, ethyl acetate, ethyl acetate/ethanol, n-propyl acetate/acetone, isopropyl acetate/ethanol, ethyl acetate/acetone and blends thereof.

Generally, this solvent will constitute from in the range of about 98 to about 80 weight percent of the coating mixture, preferably the solvent will be in the range of from 96 to 85 weight percent and most preferred in the range of from 96 to 90 weight percent (wherein the total weight percent is 100 weight percent).

When the coating contains a lactide and glycolide copolymer and a fatty acid salt or ester it is preferred that the solvent be ethyl acetate, acetone or a combination of solvents. If the solvent system is a combination of ethyl acetate/ethanol, it should contain in the range from about 99 to about 70 weight percent ethyl acetate and preferably in the range from 90 to 80 weight percent ethyl acetate. If the solvent system is a combination of ethyl acetate/acetone, it should contain in the range from about 99 to about 1 weight percent ethyl acetate and preferably from in the range of from 90 to 10 weight percent ethyl acetate. If the solvent system is a combination of n-propyl acetate/acetone, it should contain in the range from about 90 to about 25 weight percent n-propyl acetate and preferably in the range from 80 to 40 weight percent n-propyl acetate. If the solvent system is a combination of isopropyl acetate/acetone, it should contain in the range from about 65 to about 10 weight percent isopropyl acetate and preferably about 55 to about 10 weight percent isopropyl acetate.

The amount of coating composition applied to the fiber, or the coating add-on, will vary depending upon the construction of the fiber, e.g., the number of filaments and tightness of braid or twist. In general, the coating composition applied to a braid will constitute from about 0.1 to about 10 percent by weight of the coated fiber, but coating composition may range from as little as about 0.05 percent by weight to as much as about 15 percent or higher in some cases. As a practical matter, and for reasons of economy and general performance, it is generally preferred to apply the minimum amount of coating composition consistent with good tie-down performance, and this level of coating is readily determined experimentally for any particular fiber-coating system.

The coatings are applied to any suture material where it is desired to improve fiber lubricity, suture tie-down characteristics, or the like. The coating is particularly useful with synthetic absorbable multifilament sutures such as homopolymers and copolymers of glycolide, lactide (which includes L-, D-, and meso-forms of lactide and mixtures thereof), ε-caprolactone, p-dioxanone, trimethylene carbonate, 1,4-dioxepan-2-one, poly(alkylene oxalate), and mixtures of such polymers with each other and with other compatible absorbable compositions as those described; for example, in U.S. Pat. Nos. 3,636,952 and 2,683,136 which patents are herewith incorporated herein by reference. One suitable suture composition would include copolymers of p-dioxanone, trimethylene carbonate and glycolide and copolymers of lactide and p-dioxanone. Preferred are suture compositions derived from lactide and glycolide sometimes referred to herein as simply homopolymers and copolymers of lactide and glycolide and copolymers of glycolide and ε-caprolactone.

It will be readily appreciated that coatings may likewise be used with good results on absorbable monofilament sutures as well as on nonabsorbable monofilament and multifilament sutures.

Nonabsorbable sutures such as cotton, linen, silk, nylon, polyethylene terephthalate and polyolefins are normally coated with nonabsorbable compositions. Polyolefins are usually of monofilament construction while cotton, linens, silk and polyester are usually of braided, twisted or covered multifilament construction.

The coating mixture usually is applied to the final suture structure in order to provide a substantially continuous coating on at least the outward facing surfaces of the outer-most filaments of the braid. It is understood, however, that the coating mixture may be applied, if desired, to the individual filaments before they are formed into strands or to the individual strands before they are formed into the final suture structure. This invention is not limited as to suture size or composition, but may be practiced, for example, with sutures from size 9–0 to size 3 and larger, and with other suture materials. In coating multifilament sutures, it is not necessary that every filament within the suture be individually or completely coated.

The improvement in tie-down properties imparted to synthetic absorbable sutures may be determined semi-quantitatively by comparing the feel of coated and uncoated sutures during the act of tying down a single throw knot. Such comparisons are preferably made on both wet and dry sutures since many suture materials have different tie-down properties when tested wet or dry.

We claim:

1. A suture coating apparatus, comprising: a suture coating head, said suture coating head comprising a vessel suitable for containing a coating mixture having an opening suitable for passing a suture through; a first guide means for directing a suture into the coating mixture contained in the vessel; a second guide means positioned in said vessel suitable for redirecting the suture out of the coating mixture; a third guide having a surface which is adjacent to or contacts the suture and forms a meniscus that removes any excess coating entrained by the suture when it is redirected by the third guide means, wherein the third guide means comprises at least one guide roller comprising a body that has at least one side attached to the body that provides the surface to form the meniscus with the excess entrained coating.

2. The suture coating apparatus of claim 1 wherein the first guide means, the second guide means and the third guide means are attached to a frame.

3. The suture coating apparatus of claim 2 wherein the first guide means comprises one or more guide rollers positioned to orient the suture path between the first guide means and the second guide means in a substantially vertical and downward path into the vessel.

4. The suture coating apparatus of claim 3 wherein the second guide means comprises at least one guide rollers positioned to orient the suture path between the second guide means and the third guide means in a substantially vertical and upward path.

5. The suture coating apparatus of claim 4 wherein the third guide means comprises at least three guide rollers.

6. The suture coating apparatus of claim 5 wherein the first guide roller of the third guide means redirects the suture path after the second guide means from a substantially vertical and upward orientation to a substantially vertical and downward path.

7. The suture coating apparatus of claim 6 wherein the second guide roller of the third guide means redirects the suture path after the second guide roller of the third guide means from a substantially vertical and downward orientation to a substantially vertical and upward orientation.

8. The suture coating apparatus of claim 7 wherein the third guide roller of the third guide means redirects the suture path after the second guide roller of the third guide means from a substantially vertical and upward orientation to a substantially horizontal path.

9. The suture coating apparatus of claim 8 wherein the vessel is in fluid communications with a reservoir.

10. The suture coating apparatus of claim 9 wherein the vessel has an outlet in the upper section.

11. The suture coating apparatus of claim 10 wherein a diverter means is positioned above the vessel and below the third guide means to control the fluid communications into the vessel.

* * * * *

UNITED STATES PATENT AND TRADEMARK OFFICE
CERTIFICATE OF CORRECTION

PATENT NO.    : 6,187,095 B1
DATED         : February 13, 2001
INVENTOR(S)   : Samauel K. Labrecque, Vishvaroop Agarwal and Henry Pokropinski, Jr.

It is certified that error appears in the above-identified patent and that said Letters Patent is hereby corrected as shown below:

<u>Column 8,</u>
Line 23, please delete "rollers" and insert therefore -- roller --

Signed and Sealed this

Thirteenth Day of January, 2004

JON W. DUDAS
*Acting Director of the United States Patent and Trademark Office*